Nov. 11, 1941. W. BAUER Re. 21,938

PAD MAKING MACHINE

Original Filed Jan. 18, 1924 8 Sheets-Sheet 1

Nov. 11, 1941. W. BAUER Re. 21,938

PAD MAKING MACHINE

Original Filed Jan. 18, 1924 8 Sheets-Sheet 2

Inventor.
William Bauer.
Fisher, Lowe, Clapp & Soans. Attys.

PAD MAKING MACHINE

Original Filed Jan. 18, 1924 8 Sheets-Sheet 3

Inventor.
William Bauer
Fisher, Fowle, Clapp & Sears Attys

Nov. 11, 1941. W. BAUER Re. 21,938

PAD MAKING MACHINE

Original Filed Jan. 18, 1924 8 Sheets-Sheet 4

Inventor
William Bauer
Fisher, Fowle, Claff & Soans Attys

Nov. 11, 1941. W. BAUER Re. 21,938

PAD MAKING MACHINE

Original Filed Jan. 18, 1924 8 Sheets-Sheet 5

Inventor.
William Bauer
Fishe, Fowle, Clapp & Soare Attys

Nov. 11, 1941. W. BAUER Re. 21,938
PAD MAKING MACHINE
Original Filed Jan. 18, 1924 8 Sheets-Sheet 6
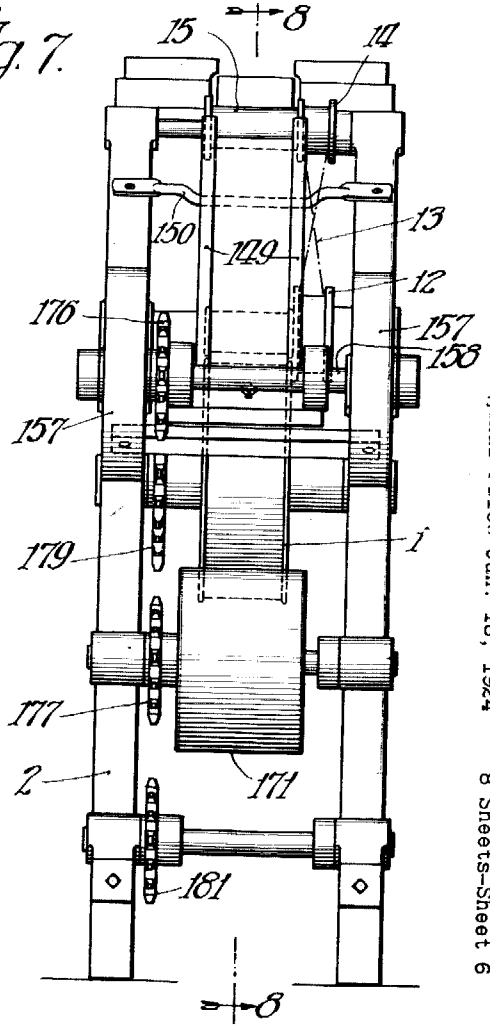
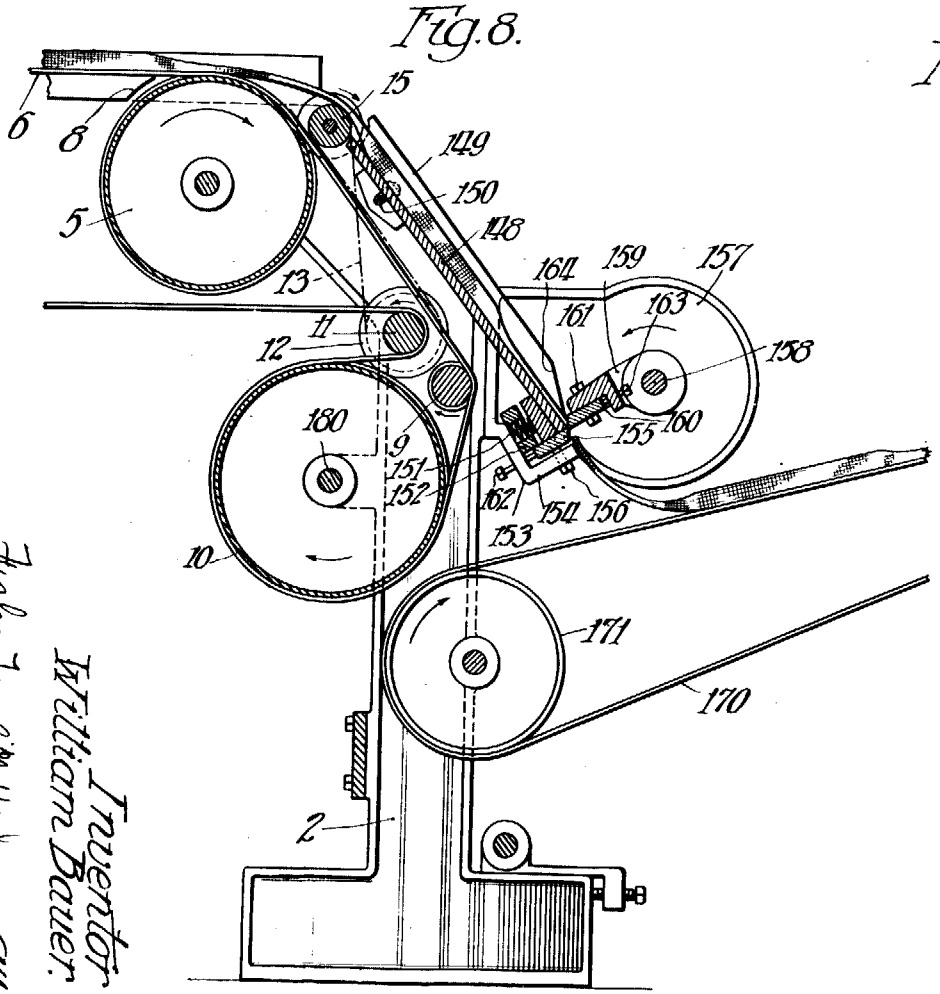
Inventor
William Bauer.
Fisher, Fowle, Clapp & Boam Attys.

Nov. 11, 1941. W. BAUER Re. 21,938

PAD MAKING MACHINE

Original Filed Jan. 18, 1924 8 Sheets-Sheet 7

Inventor:
William Bauer.
Fisher, Fowle, Clapp & Sears Attys.

Nov. 11, 1941. W. BAUER Re. 21,938

PAD MAKING MACHINE

Original Filed Jan. 18, 1924 8 Sheets-Sheet 8

Inventor.
William Bauer.

Hisha, Towle, Clapp & Sears Attys.

Reissued Nov. 11, 1941

Re. 21,938

UNITED STATES PATENT OFFICE 21,938

PAD MAKING MACHINE

William Bauer, Neenah, Wis., assignor, by mesne assignments, to International Cellucotton Products Co., Chicago, Ill., a corporation of Delaware Original No. 1,794,358, dated March 3, 1931, Serial No. 687,012, January 18, 1924. Application for reissue February 25, 1938, Serial No. 192,585

25 Claims. (Cl. 154—29)

My invention relates to machines for making catamenial bandages and the like wherein a pad of soft filling material is enclosed in a wrapper of gauze or other suitable material.

The principal objects of my invention are to make and cover pads of this character rapidly and with very little labor or expense; to automatically cut and wrap the pad; to apply the wrapper so as to leave loose ends projecting beyond the ends of the pad; to provide means for satisfactorily cutting a comparatively thick layer of soft absorbent material; and in general, to provide a simple, dependable machine which operates practically without attention except to renew the stock from which the pads are made.

Figure 1:
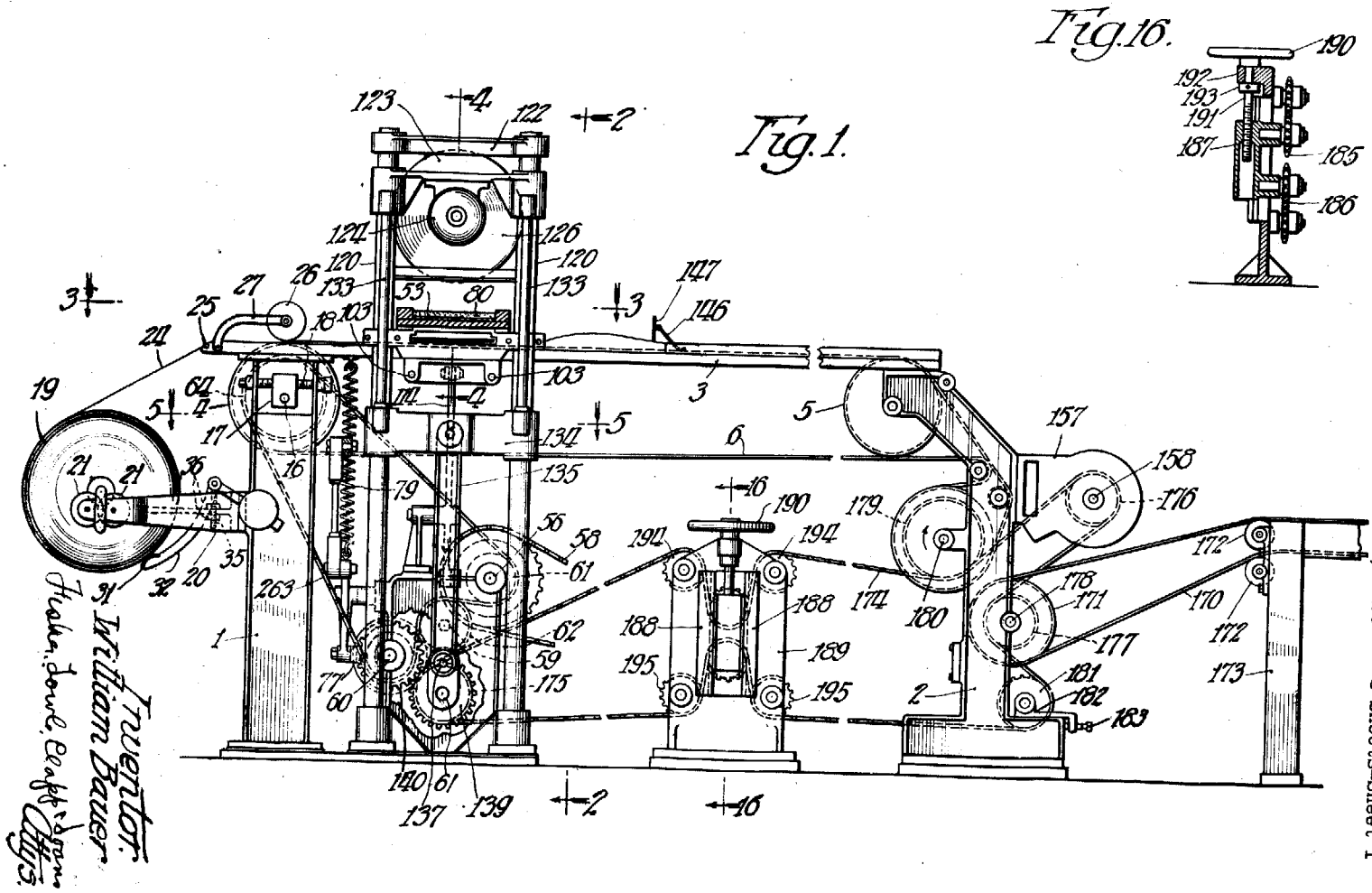
Figure 2:
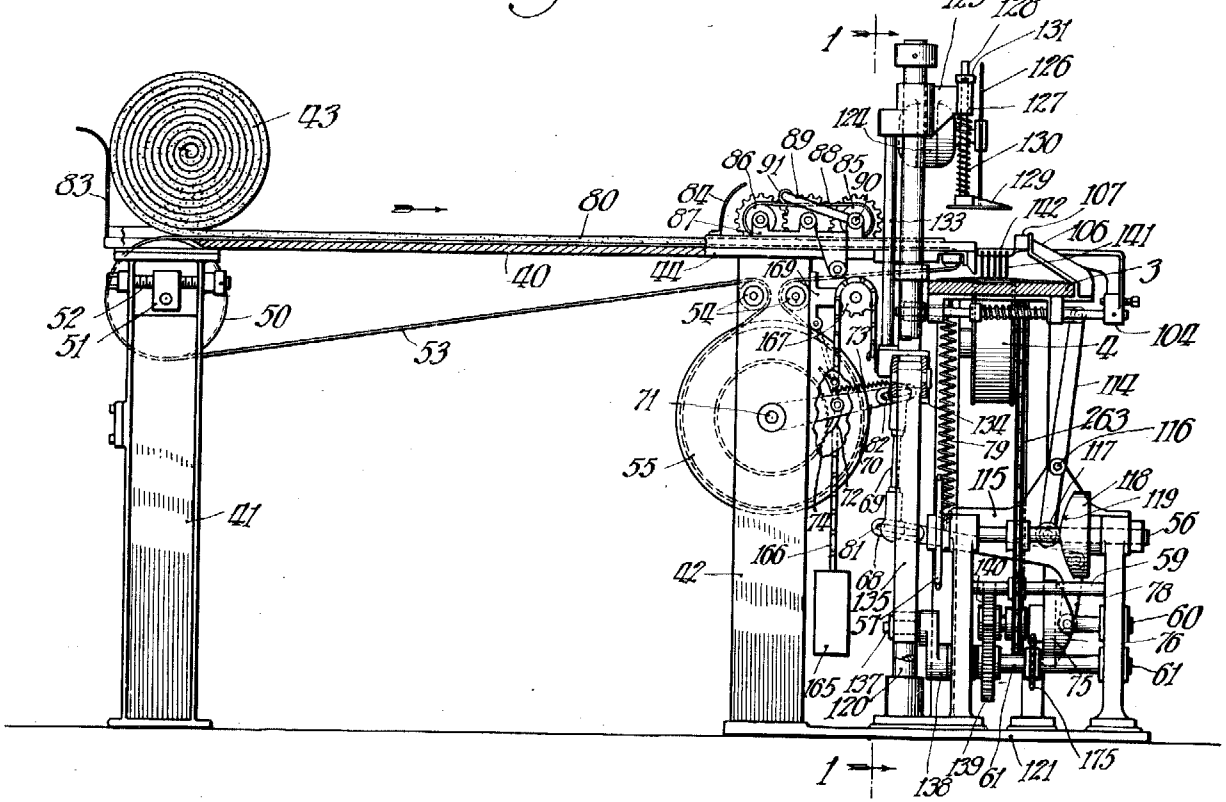
Figure 3:
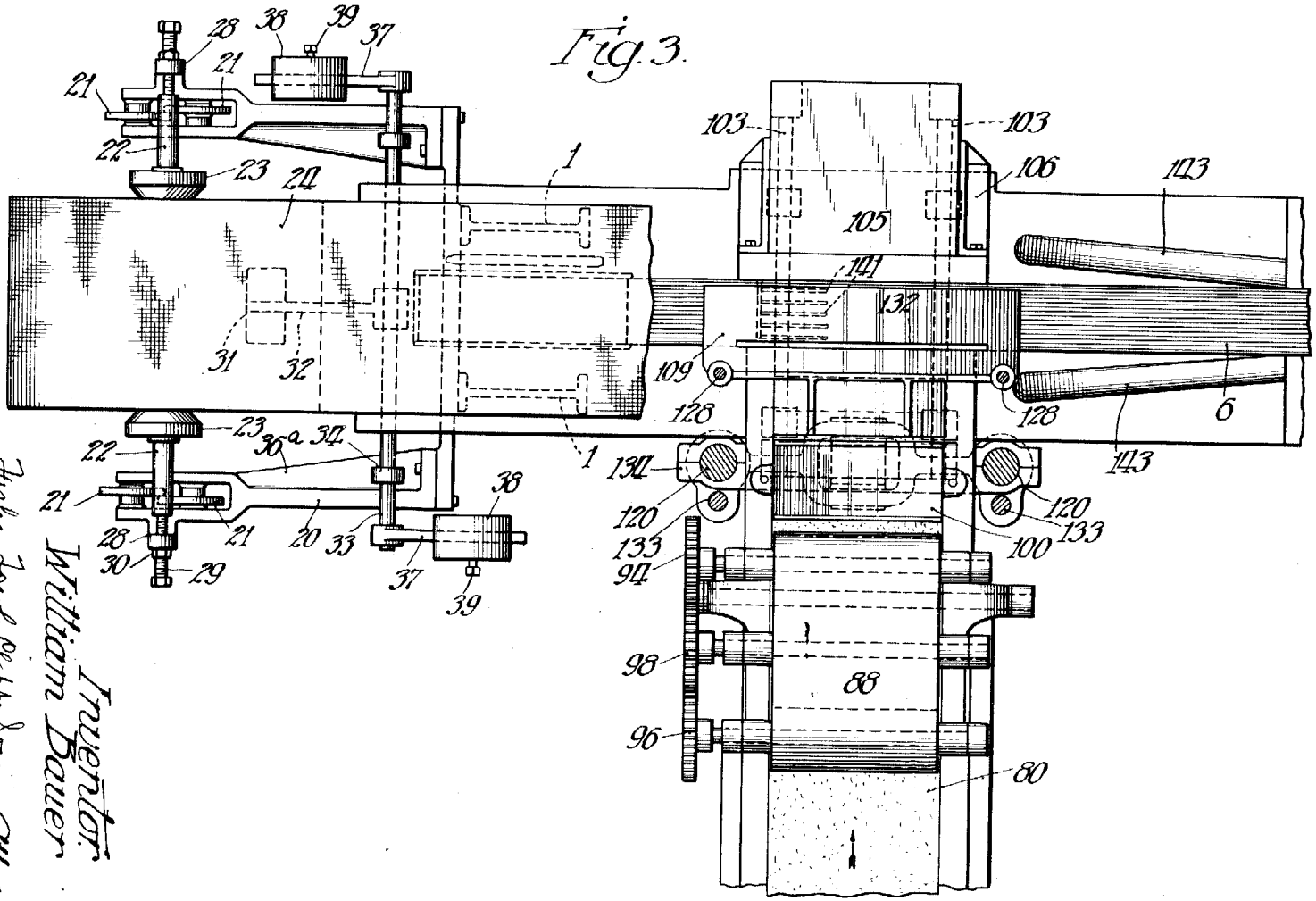
Figure 4:
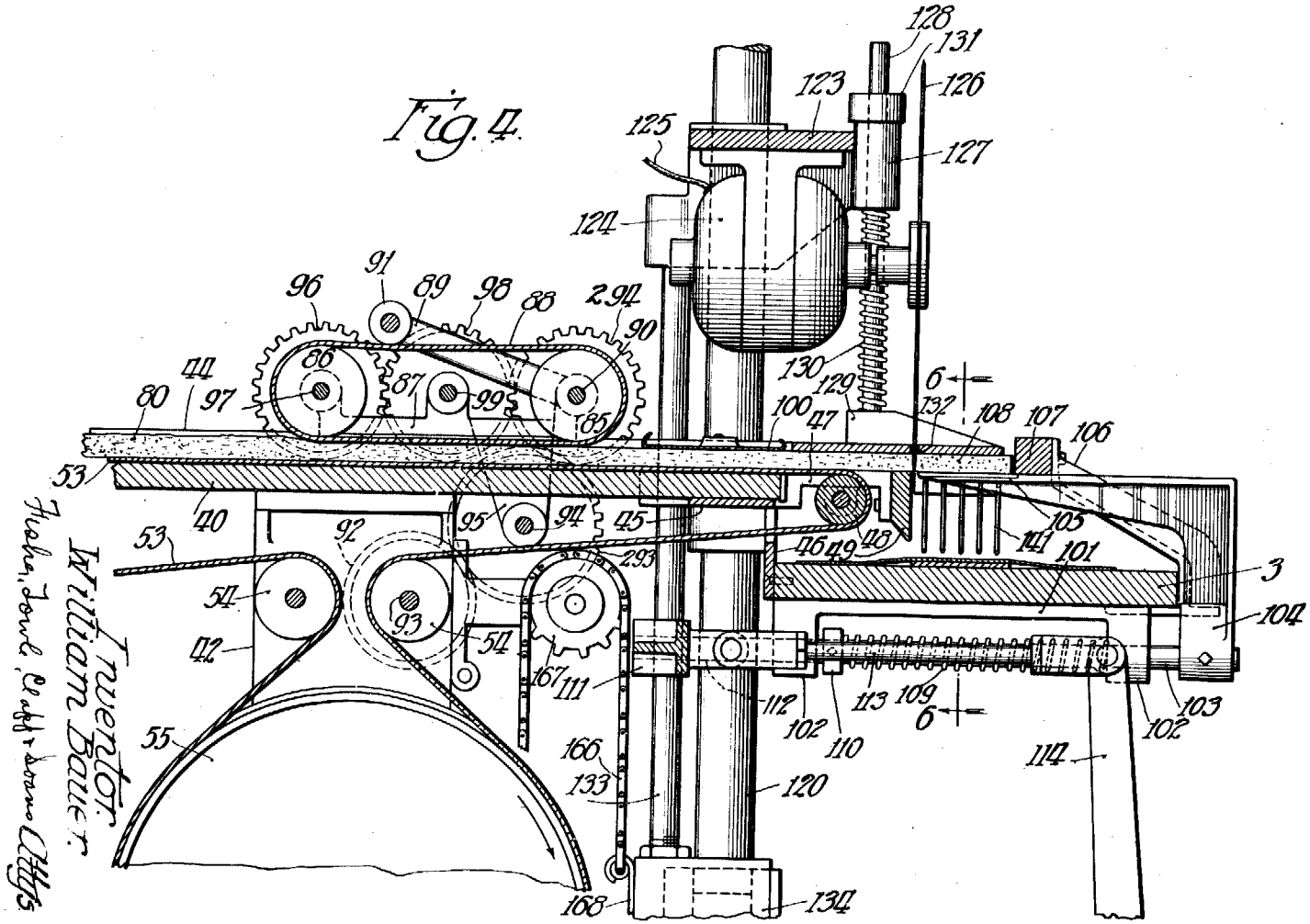
Figure 5:
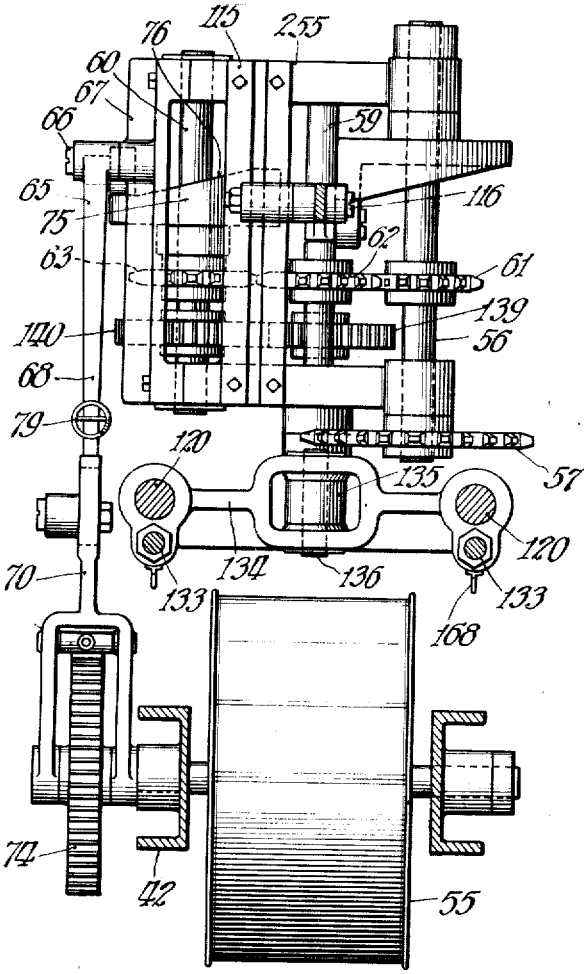
Figure 6:
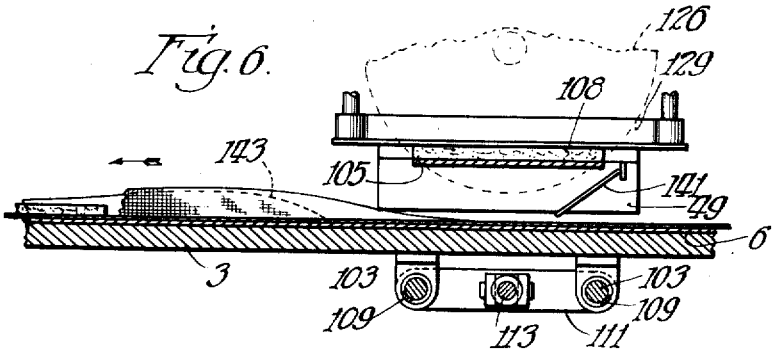
Figure 9:
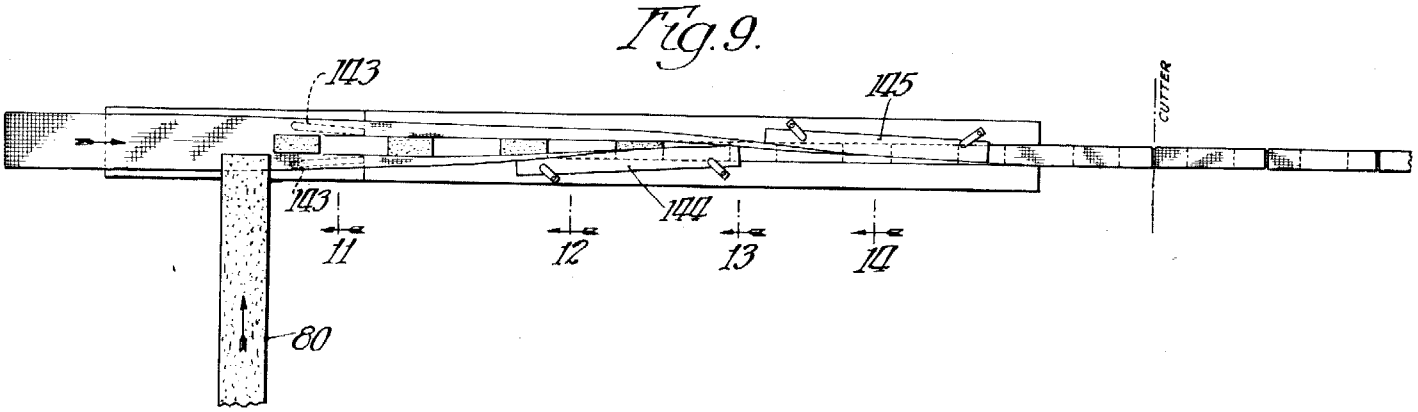
Figure 10:
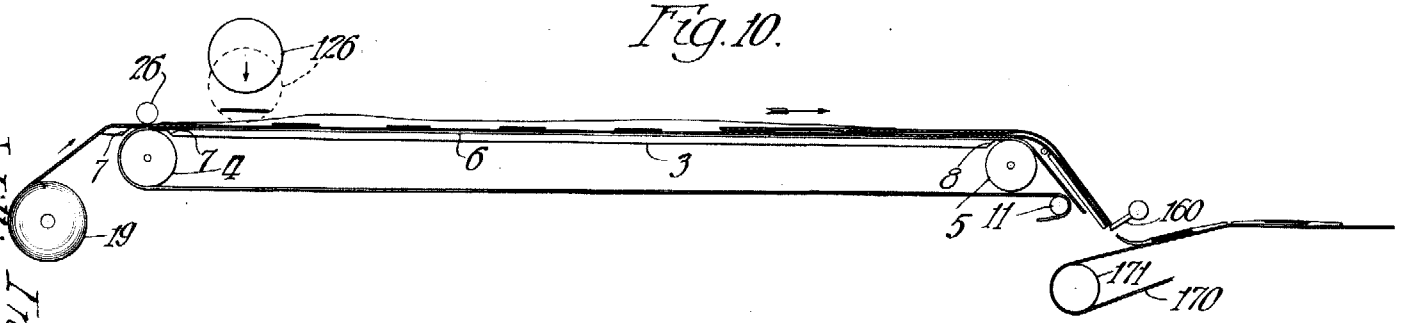
Figure 15:
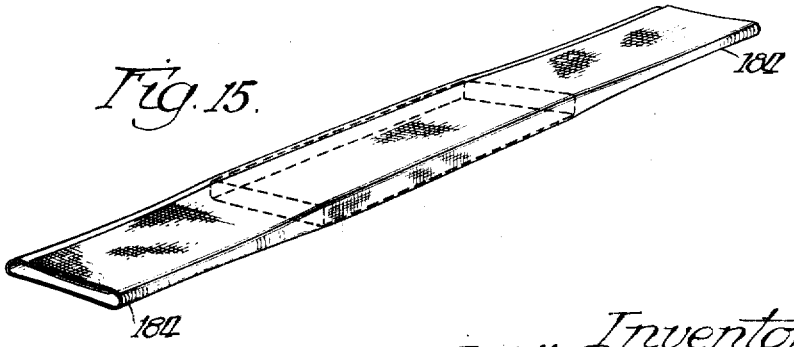

On the drawings:

Fig. 1 is a side view, partly in section on the line 1—1 of Fig. 2, of a pad making machine embodying my improvements;

Fig. 2, a view of the machine taken on the line 2—2 of Fig. 1, and with a part of the filler feeding table in section;

Fig. 3, an enlarged top view of a portion of the machine on the line 3—3 of Fig. 1, with parts broken away to disclose the details of the construction;

Fig. 4, an enlarged detail view in section on the line 4—4 of Fig. 1;

Fig. 5, an enlarged detail view partly in section on the line 5—5 of Fig. 1;

Fig. 6, a detail sectional view on the line 6—6 of Fig. 4;

Fig. 7, a view looking at the delivery end of the machine;

Fig. 8, a sectional view of said end of the machine taken on the line 8—8 of Fig. 7;

Figs. 9 and 10, diagrammatic top and side views, showing the progress of the pads through the machine, the latter view being partly in section;

Figs. 11, 12, 13 and 14, enlarged sectional views on the lines 11—11, 12—12, 13—13 and 14—14 respectively of Fig. 9;

Fig. 15 is a perspective view of the completed pad; and

Fig. 16, a sectional view on the line 16—16 of Fig. 1, of the synchronizing mechanism for regulating the point of severance of the wrappers of adjoining pads.

Referring to the drawings, the reference numerals 1 and 2 indicate respectively the two end standards of the machine which have the plate 3 extending between and secured to the upper ends thereof. Pulleys or drums 4 and 5 are journaled respectively at the upper ends of the standards 1 and 2 and carry the belt 6, the upper length of which runs over the plate 3. The plate 3 is provided with an opening 7 therethrough adjacent one end to receive the upper portion of the pulley 4 so that the upper extremity of the pulley is substantially flush with the upper surface of the plate, and the other end of the plate 3 is notched as indicated at 8 to likewise accommodate the pulley 5. The belt 6, at the delivery end of the machine, passes over an idler 9, around an idler 10 and is looped around another idler 11, all of which are journaled in the standard 2, and the idler 11 has a belt pulley 12 secured to one end thereof and connected by the crossed belt 13 to a smaller pulley 14 on a stripper roll 15 which is journaled at the upper end of the standard 2. The folding of the belt around the idler 11 affords a substantial frictional engagement to insure a positive drive of the roll 15 which is driven in the same direction but at a faster surface speed than the belt 6 and serves to divert the strip of material, carried along by the belt, from the latter to a cutting device which will be presently explained.

For regulating the tension of the belt 6, the shaft 16 which carries the roll 4 is journaled in bearing blocks 17 which are mounted on screws 18 at the upper ends of the standard 1, so that by turning the screws 18 the bearing blocks 17 and roll 4 carried thereby are adjustable to and from the other roll 5.

The belt 6 serves to propel a strip of pad covering material such as a gauze, along the upper surface of the plate 3 from the roll 19 which is carried at the outer ends of the brackets 20 which project forwardly from the standard 1. For the purpose of permitting the roll 19 to turn freely, a pair of anti-friction rollers 21 are journaled at the outer end of each bracket 20 and support the spindle or shaft 22 of the spool 23 upon which the roll of gauze or other covering material is wound.

The strip of covering material, which is indicated at 24, is wider than the belt 6 as shown in Fig. 3, and is led up over the rounded end edge 25 of the plate 3 under a roll 26 which is directly above the roll 4 and serves to hold the gauze against the belt 6 as it runs over the top of the roll 4, and from this roll the strip of gauze is led past the mechanism which deposits a pad of filling material thereon, then through folding devices which fold the side portions of the gauze strip over the pads thereon, and is then taken off the belt by the stripper roll 15 and fed through a cutter which severs the gauze at points midway between successive pads.

The roll 26 is journaled in the outer ends of a pair of arms 27 which are pivoted respectively to the opposite sides of the plate 3 near the end so that the roll acts by gravity to exert the desired pressure on the gauze. For adjusting and holding the roll 19 so as to feed the strip of gauze in proper alignment with the pad feeding and strip folding mechanisms, each of the brackets 20 is provided with a laterally and upwardly extending arm 28 near the outer end (see Fig. 3), through which an adjusting screw 29 is threaded so as to engage against the end of the shaft 22, a lock nut 30 being provided on each adjusting screw to hold the latter in the adjusted position.

A shoe 31 is arranged to bear against the periphery of the roll 19 to impose a slight tension on the strip 24, and is carried at the outer end of an arm 32 which is fixed on a shaft 33 carried by bearings 34 at the inner ends of the brackets 20. These bearings are formed with threaded stems 35 which are inserted through apertures in the horizontal web 36a of the respective brackets, and may be adjusted to various elevations by the lock nuts 36 which are threaded thereon at opposite sides of the web 36a. The shaft 33 has arms 37 at the opposite ends thereof and extending at opposite sides of said shaft, and upon these arms are mounted adjustable weights 38 which may be secured in various positions of adjustment by the set screws 39. With this construction the weights may be adjusted to afford the desired pressure of the shoe 31 against the roll 19 and the two weights afford sufficient inertia to prevent the shoe 31 being thrown away from the surface of the roll 19 by irregularity in the surface of the latter.

Referring now to the mechanism for forming the pads and depositing same on the strip 24 of gauze or other covering material, a feed table 40 is mounted on a pair of standards 41 and 42 at right angles to and somewhat above the plate 3 and has the inner end or an extension thereof projecting over the plate 3, as shown in Figs. 2 and 4, and the table supports a roll 43 of soft filling material which is confined on the table 40 between guides 44 along the side edges of the table 40. The extreme inner end of the table 40 is carried by a bracket 45 which has a depending plate portion 46 secured to the adjoining edge of the plate 3 as shown in Fig. 4, said bracket being provided with side extensions 47 with depending bearings in which a roll 48 is journaled, and the outer ends of these extensions 47 have a plate 49 secured thereto with the face thereof lying in a vertical plane substantially coinciding with the near edge of the belt 6. At the outer end of the table 40 is a roll 50 which is journaled in adjustable bearings 51 carried by screws 52, mounted on the standards 41 for adjusting the roll 50 in the same manner as the roll 4 hereinbefore described. A belt 53 passes around the rolls 50 and 48 so that the upper length runs over the upper surface of the table 40 between the guides 44, while the lower length of the belt passes around a pair of idler rolls 54 on the standard 42, and is looped around a drum 55 which is also journaled in the standards 42.

Mounted under the plate 3 is a frame 255 carrying the driving mechanism for the machine. This frame has the main driving shaft 56, journaled therein, upon which is fixed a sprocket 57 which is connected by the link belt 58 to any suitable source of power. A number of shafts 59, 60 and 61 are also journaled in the frame 255 in parallel relations to the main shaft 56, and the shafts 56, 59, and 60 have the sprockets 61, 62 and 63 respectively fixed thereon and engaged by the chain 263 as indicated in Fig. 1, whereby the shafts 59 and 60 are driven from the main shaft, and this chain extends upwardly around a sprocket 64 which is fixed on the shaft 16 for driving the roll 4 and belt 6. A bell crank 65 is pivoted at the elbow, as indicated at 66, on a cross brace 67 of the frame 255, and has the outer end of the arm 68 thereof connected by the link 69 to the outer end of the arm 70 which is pivoted at its inner end on a shaft 71, which carries the drum 55. A pawl 72 is pivoted on the arm 70 and held by the spring 73 in engagement with a ratchet wheel 74 which is connected to rotate with the drum 55 so that the oscillation of the arm 70 serves to advance the drum 55 with a step by step movement. For rocking the bell crank 65, a cam disk 75 is secured on the shaft 60 and provided with a cam face 76 which cooperates with a roller 77 on the lower end of the arm 78 of the bell crank 65, said roller being held against the cam face by a spring 79 which has one end connected to the arm 68 and the other end connected to the underside of the plate 3. The cam mechanism, which I have just described, serves to intermittently operate the belt 53 to feed the strip 80 of filling material from the roll 43 to a cutter which severs the proper amount therefrom to form the filling pad. For the purpose of adjustment to permit proper engagement of the pawl 72 with the teeth of the ratchet wheel 74, the link 69 is preferably in the form of a turnbuckle, with eye members threaded on the ends so that the length of the link may be varied as required, and the eye members on the ends of the link 69 are pivoted on pins which are adjustably locked in slots 81 and 82 in the outer ends of the arms 68 and 70 respectively so that the throw of the arm 70 may be regulated to vary the extent to which the strip 80 is advanced upon each operation of the arm 68.

The roller 43 of filling material is not mounted on a fixed axis but is merely confined between abutments 83 and 84, the former of which is secured to the outer end of the table 40 and the latter of which is secured to the guides 44 and bridges the strip 80 of filling material and the belt 53 on the table 40.

For holding the strip 80 of filling material against the belt 50 adjacent the delivery end of the latter so as to insure a positive feed of the said strip, a pair of rolls 85 and 86 is mounted in spaced relation on brackets 87 which are carried by the guides 44, and have a belt 88 passed therearound so that the lower length of the belt engages the upper surface of the strip 80 and holds the latter close against the belt 53. A pair of arms 89 which is pivoted on opposite ends respectively of the shaft 90, which carries the roll 85, have the roll 91 journaled in the outer ends thereof and resting on the upper length of the belt 88 to serve as a belt tightener.

For operating the belt 88, there is a gear 92 fixed on the shaft 93, to which the idler roll 54 is attached, and this gear meshes with a gear 293 on a shaft 94 which is journaled in hangers 95, depending from the brackets 87, and this gear 293 meshes with a gear 294 which is fixed on the shaft 90 to which the roll 85 is fixed. A similar gear 96 is secured to the shaft 97, to which the roll 86 is attached, and the gears 294 and 96 mesh with an intermediate gear 98 which is mounted on a shaft 99 journaled in intermediate bearings of the bracket 87.

Immediately beyond the location of the belt 88 is a cover plate 100 which is mounted on the guides 44 and extends over the strip 80 of filling material, for holding the latter down against the belt 53, said plate being provided with rounded edges as shown in Fig. 4 so that the filling material readily slides thereunder.

Mounted on the under side of the plate 3 are spaced brackets 101, each of which has a pair of depending bearings 102 in which a shaft 103 is mounted for axial sliding movement. A bracket 104 is secured on the outer end of each rod and projects upwardly and inwardly over the plate 3, and these brackets have a plate 105 secured to the inner ends thereof so that the upper surface of the plate is in the plane of the upper surface of the upper length of the belt 53, and this plate serves as a temporary support for the end of the strip 80 during the operation of severing the end portion from the strip. A pair of brackets 106 is secured to the outer edge of the plate 3 and extends upwardly and inwardly thereover with the brackets 104 interposed therebetween, and these brackets 106 have a block 107 secured to their inner ends just above the plate 105 for stripping the severed pad 108 from the plate 105 when the latter is withdrawn from underneath the pad 108. A spring 109 surrounds each shaft 103 and is compressed between the outer bearing 102 and an adjustable collar 110 on the shaft 103 to normally hold the brackets 104 and plate 105 at the inward limit of movement thereof, as indicated in Fig. 4, and the inner ends of these shafts beyond the inner bearings 102 are connected to a cross head 111. A pivot lug 112 is formed in the cross head 111 midway between the shafts 103 and is connected by the link 113 to the upper end of a rocker arm 114 which is pivoted intermediate of its ends to a cross member 115 by means of a pivot pin 116. The lower end of this rocker arm 114 has a friction roll 117 thereon which is held by the springs 109 against the side of the cam disk 118 which is fixed on the shaft 56, and has the raised cam edge 119 operating at the proper time to withdraw the plate 105 from under the severed pad 108.

A pair of guide posts 120 is mounted on the base 121 adjacent the frame 255 and extends upwardly at opposite sides respectively of the table 40, and have the upper ends connected together by the brace 122. These posts serve as a guide for a vertically reciprocable cutter which is carried by a cross head 123 which has bearings at each end slidingly engaging the posts 120. A motor 124 is mounted on this cross head 123 and may be connected by means of flexible conductors 125 or otherwise to a source of current so as to operate continuously. A rotary cutter 126 is secured to the armature shaft of the motor 124 so that the inner face thereof barely clears the outer face of the plate 49, when the cutter is depressed, and said cutter comprises a thin disk with a knife edge which has been found particularly well adapted to make a clean cut through the soft filling material with which this machine is adapted to be used. A pair of spaced bearings 127 is formed on the cross head 123 at opposite sides respectively of the motor 124 to slidingly receive the shafts 128, to the lower ends of which is secured a shoe 129. Each shaft 128 has a spring 130 thereon interposed between the bearing 127 and the shoe 129 for resiliently holding the shoe in the lowermost position which is determined by collars 131 which are adjustably secured on the upper ends of the shafts 128 above the bearings 127. This shoe 129 is of a suitable width to extend substantially from the outer edge of the guide 100 to the block 107, as shown in Fig. 4, and serves when the cross head 123 is depressed, to resiliently clamp the end portion of the strip 80 of filling material on the plate 105, the outer end of the belt 53 and adjacent portions of the framework over which the strip 80 passes, and this shoe has a slot 132 through which the cutter 126 is projected after the movement of the shoe 129 is interrupted by coming in contact with the upper surface of the strip 80.

The cross head 123 is connected by a pair of parallel rods 133 to a lower cross head 134 which likewise slides on the posts 120 and is located underneath the table 40. This crosshead 134 is divided intermediate of the ends to receive the upper end of the link 135 therebetween which is pivoted on the pin 136, which latter has the ends engaged in the opposite sides of the divided portion of the cross head. The lower end of this link 135 is pivoted to the crank pin 137 of the crank 138 which is secured to the outer end of the shaft 61, which shaft is driven by means of the gear 139 which is fixed thereon and meshes with the gear 140 which is fixed on the shaft 60. By reason of this connection, the continuously driven cutter 126 and shoe 129 is reciprocated to and from the supported end of the strip 80, the parts being so timed that the strip 80 is intermittently advanced, being fed forward while the plate 105 is in the position shown in Fig. 4, whereupon the advance movement of the strip 80 is interrupted while the cutter is depressed to cut off a portion 108 from the end of the strip, after which the cutter and shoe are elevated and the plate 105 withdrawn to permit the severed pad 108 to drop down onto the continuously moving strip 24 of gauze or other wrapping material. Immediately after the pad 108 is discharged as aforesaid, the plate 105 is returned to the position shown in Fig. 4 and the strip 80 advanced another step, whereupon the cutter again descends.

To facilitate the vertical reciprocation of the cutting mechanism, a counterweight 165 is provided therefor, which is carried by a chain 166 which is passed over an idler 167 and connected to a hook 168 on the lower cross head 134. The idler 167 is mounted on brackets 169 which are secured to the standard 42.

In order to insure proper deposit of the pad 108 onto the moving strip 24 of gauze or other covering material, it is desirable that the forward end of the pad should come in contact with the moving strip 24 before the rear end thereof comes in contact therewith, and to accomplish this result a plurality of inclined guides 141 are secured to a bracket 142 which is mounted at the rear end of the strip 107 so as to incline downwardly and forwardly under the rear end of the pad 108. These guides or fingers retard the dropping down of the rear end of the pad until the forward end thereof engages the moving strip 24 and is drawn forwardly thereby.

Figure 11:
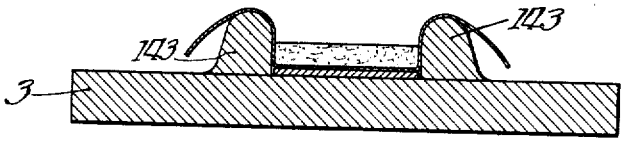
Figure 12:
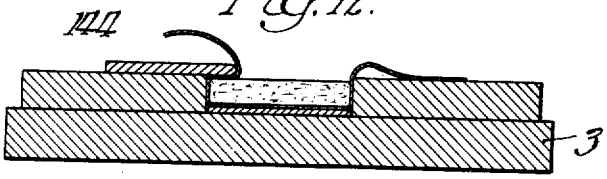
Figure 13:
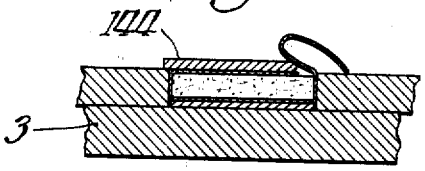
Figure 14:
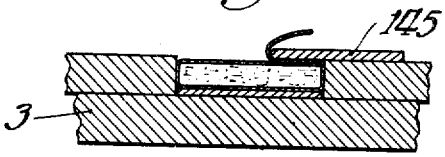

After the pads 108 are deposited on the strip 24, they are carried by said strip and the belt 6 between folding members 143 which are mounted on the plate 3 at opposite sides of the belt 6, and serve to fold up the side portions of the strip 24 in the manner shown in Fig. 11, against the side edges of the pads 108. Beyond the folders 143 are successively arranged folder plates 144 and 145 positioned respectively at opposite sides of and extending over the belt 6 at a suitable elevation to first fold one side of the strip 24 over the pads 108 and then fold the other side thereover as shown in Figs. 9 and 11 to 14 inclusive, with the opposite sides of the strip 24 overlapped over the pads. A shoe 146 may, if desired, be pivoted on a bridge 147 over the belt 6 near the delivery ends of the folders 143 to prevent overthrow of the side portions of the strip 24 before the side portions reach the folders 144 and 145.

Mounted on the standards 2 at the delivery end of the machine is an inclined chute 148 which has the upper end positioned adjacent the stripping roll 15 so that the latter delivers the folded strip 24 and enclosed pads onto this chute between the guides 149 which are secured to the side edges of the chute. This chute is pivoted near the upper end on a hanger 150 which has the ends secured to the standards 2, and the lower end of this chute is resiliently supported by one or more springs 151 which are seated in a block 152 carried by a bracket 153. This bracket has a ledge 154 beyond the end of the chute 148 to which a shear blade 155 is adjustably secured by the cap screws 156. This shear blade extends across the end of the chute 148, and the cutting edge is normally below the outer surface of chute 148 in the position in which the latter is normally held by the springs 151, the parts being so arranged that the folded strip 24 and pads therein readily pass off the end of the chute 148 without interference from the shear blade 155.

A pair of brackets 157 is secured to the standards 2 and have a shaft 158 journaled thereon and the shaft is provided with a cutter head 159, to which a shear blade 160 is secured by bolts 161 so as to swing around with the shaft 158. This shear blade 160 cooperates with the shear blade 155 to sever the folded strip 24 at predetermined intervals. Proper adjustment of the shear blades 155 and 160 is effected by adjusting screws 162 and 163.

Inasmuch as the lower end of the chute 148 is normally raised slightly above the cutting edge of the shear blade 155, it is necessary to depress the lower end of the chute at the time of the shearing operation, and to this end the cutter blade 160 is extended somewhat beyond the sides of the chute 148, and the guides 149 at their lower ends are beveled as indicated at 164, so that as the cutter 160 nears the cutting position, it engages the beveled edges 164 of the guides and depresses the lower end of the chute 148 sufficiently against the tension of the springs 151 so that the cutting edges of the shear blades may cooperate.

The cutter 160 is rotated at a rate of speed corresponding to the rate of movement of the folded strip 24 so that as the cutter comes to the cutting position, it neither retards nor pulls on the strip, and moreover, the cutter 160 is disengaged from the lower end of the chute 148 as the shearing operation takes place, and thereby permits the immediate elevation of the lower end of the chute 148 so that the leading end of the folded strip 24 is readily advanced over beyond the cutter 155.

For conveying the severed pads away from the lower end of the chute 148, I have provided a conveyer belt 170 which passes around a drum 171 on the standards 2 and over idlers 172 on a standard 173 so that the upper length of this belt passes under the lower end of the chute 148 in the direction indicated in Fig. 8. This conveyer and cutter 159 are both driven by a chain 174 which passes around and is driven by a sprocket 175 on the shaft 61, said chain being guided around the sprocket 176 on the cutter shaft 158 and the sprocket 177 on the shaft 178 of the drum 171 by an idler 179 on the shaft 180 which carries the drum 10 and the sprocket 181 which is carried by adjustable brackets 182 on the standards 2. Adjusting screws 183 are provided in connection with the brackets 182 for regulating the tension of the driving chain 174.

In the operation of this machine, the pads 108 are deposited at regular intervals on the strip 24 of gauze so that a considerable length of gauze intervenes between successive pads so as to leave loose ends of the enclosing gauze on each pad as shown in Fig. 15. It is desirable to cut the gauze midway between the successive pads so that the loose ends 184 are of uniform length, and this necessitates the synchronizing of the cutter 160 with the mechanism which advances the strip 24 and particularly with the mechanism which severs and deposits the pads 108 onto the moving strip 24. In order that these mechanisms may be properly synchronized, the upper and lower lengths of the chain 174 are passed respectively under and over idler sprockets 185 and 186 which are adapted to be simultaneously raised or lowered to vary the time of the cutting operation of the cutter 160 with respect to the strip feeding mechanism and the pad depositing mechanism. These sprockets 185 and 186 are journaled in a block 187 which slides between the guides 188 of the standard 189, and is adapted for vertical adjustment by a hand wheel 190 which has a stem 191 journaled in an offset bearing 192 of the standard 189 and held against axial movement by engagement of the bearing 192 between the hub of the hand wheel 190 and the collar 193 on the stem. The lower end of this stem 191 is threaded and engages a threaded aperture in the block 187 so that by turning the hand wheel 190 the block 187 and sprockets 185 and 186 are raised and lowered. Idlers 194 are journaled on the standard 189 above and at opposite sides of the sprocket 185 and have the upper length of the chain 174 passed therearound, as shown in Fig. 1, and similar idler sprockets 195 are mounted on the standard 189 at opposite sides of and below the sprocket 186 to engage the lower length of the chain 174 in a similar manner. By this arrangement, it will be observed that when the hand wheel 190 is turned so as to raise the block 187 and the sprockets 185 and 186, the upper length of the chain 174 is shortened while the lower length is correspondingly taken up, and this results in a backing up of the cutter 160 so that the cutting operation is delayed, while operation of the hand wheel 190 in the reverse direction in a similar manner advances the operation of the cutter 160. Thus the point between the ends of the successive pads 108 at which the strip 24 is severed may be accurately regulated so that the loose ends 184 are of a uniform length.

While I have shown and described my invention in a preferred form, I am aware that various changes and modifications may be made without departing from the principles of my invention, the scope of which is to be determined by the appended claims.

I claim:

1. In a machine for making sanitary napkins, the combination of means for intermittently advancing a strip of fibrous, soft, absorbent filling material, a continuously rotated cutter, means for reciprocating the cutter to and from the strip of filling material so as to intermittently sever predetermined portions of the latter to form pad sections, and a wrapping device for folding a wrapper of cotton gauze around each pad section.

2. In a machine for making sanitary napkins, the combination of mechanism for feeding a strip of fibrous, soft, absorbent filling material, a shoe reciprocable to and from the strip of filling material for intermittently holding the latter, a cutter cooperating with the shoe to sever a portion of the filling material as the latter is held by the shoe so as to form pad sections, and means for enclosing the pad section in a wrapper of cotton gauze.

3. In a machine for making sanitary napkins, the combination of feeding mechanism for advancing a strip of cotton gauze, mechanism for feeding a strip of fibrous, soft, absorbent filling material over the strip of gauze, a holder movable to and from a position above the strip of gauze for supporting an end portion of the strip of filling material, a cutting device adapted to sever the supported end portion of the strip of filling material, means for withdrawing the support so as to deposit the severed portion of filling material onto the strip of gauze, and folding devices for folding the side portions of the gauze over the severed portion of the filling material.

4. In a machine for making sanitary napkins, the combination of an elongated support, a conveyer belt operable lengthwise over the support, means for supporting a roll of gauze adjacent one end of the support, a pressure roll above the receiving end of the belt and cooperating with the latter to feed the strip of gauze from the roll lengthwise over the surface of the support, means for supplying and depositing a pad of fibrous, soft, absorbent filling material at predetermined intervals onto the strip of gauze as the gauze is advanced along the surface of the support, folders at opposite sides of the belt for overlapping the side portions of the gauze over the pads of filling material, and a cutting device for severing the folded gauze intermediate of successive pads.

5. In a machine for making sanitary napkins, the combination of a conveyer belt, means for supplying a strip of gauze to the belt, pad depositing mechanism cooperating with the conveyer belt to deposit pads at spaced intervals on the strip of gauze as the gauze is advanced by the belt, folding devices for turning the side portions of the strip of gauze over the upper surfaces of the pads, a stripper roll at the delivery end of the conveyer belt for removing the folded strip of gauze and enclosed pads from the conveyer belt, and a cutter beyond the stripper roll for severing the folded strip of gauze intermediate of successive pads.

6. In a machine for making sanitary napkins, the combination of a conveyer belt, means for supplying a strip of cotton gauze to the receiving end of the belt, depositing mechanism for depositing pads at intervals on the strip of gauze, folders for folding the side portions of the strip of gauze over the pads, a stripper roll at the delivery end of the belt for removing the folded strip of gauze and pads from the belt, and mechanism for operating the stripper roll at a higher surface speed than the belt.

7. In a machine for making sanitary napkins, the combination of means for advancing a strip of gauze, a shiftable support above the path of movement of the strip of gauze, feeding mechanism adapted to supply pads of fibrous, soft, absorbent filling material successively to the shiftable support, mechanism for withdrawing the shiftable support after each pad has been placed thereon so as to deposit said pad by gravity onto the strip of gauze, and retarding means for holding the rear end of the pad away from the moving strip of gauze until the forward end of said pad engages and is moved forward by the moving strip of gauze.

8. In a machine for making sanitary napkins, the combination of means for advancing a strip of cotton gauze, an elongated support adjacent the path of movement of the strip of gauze, a belt operable lengthwise over the elongated support and having a rotary member thereabove and cooperating therewith to feed a layer of fibrous, soft, absorbent filling material therebetween onto the strip of gauze, guides at opposite sides of the support, and means spaced lengthwise of the support for loosely confining a roll of filling material on the support and permitting said roll to unwind as the filling material is fed onto the strip of gauze.

9. In a machine for making sanitary napkins, the combination with mechanism for enclosing quantities of fibrous, soft, absorbent filling material at intervals in a continuous strip of gauze, of a yieldable support for said strip, a shearing element adjacent said support, and a rotary cutter adapted to simultaneously deflect the support and cooperate with the first mentioned shearing element to sever the moving strip of gauze between the enclosed quantities of filling material.

10. In a machine for making sanitary napkins, the combination of mechanism for advancing a strip of gauze, depositing means for supplying pads of fibrous, soft, absorbent filling material at spaced intervals onto the strip of gauze, folding devices for folding the side portions of the strip of gauze over the pads, a stationary cutter and a movable cutter for severing the folded strip of gauze between the pads, and means for affording a relative movement between the stationary cutter and the severed edge of the folded strip of gauze whereby the severed end of the folded strip of gauze is freed from the stationary cutter and adapted to advance therebeyond.

11. In a machine for making sanitary napkins, the combination of means for propelling a strip of gauze, means for depositing quantities of fibrous, soft, absorbent filling material at intervals on the gauze, folding devices for folding side portions of the gauze over the separated portions of filling material, a cutter for severing the folded strip of gauze, driving mechanism for the strip propelling and filler depositing means and the cutter, and means for adjusting the relation between the cutter operating mechanism and the other strip propelling and filler depositing means so as to vary the point between the successive portions of filling material at which the folded strip of gauze is severed.

12. In a machine for making sanitary napkins, the combination of a depressibly mounted chute and a cutter member disposed adjacent one end thereof, the operative face of said chute adjacent said cutter member being normally elevated above said cutter member.

13. In a machine for making sanitary napkins, the combination of a chute and a cutting device comprising a pair of relatively movable blades, one of said blades being mounted adjacent the delivery end of said chute, said last named blade and chute being mounted to permit relative movement whereby normally the chute is operative to feed material between said cutters, said relative movement being effected when the cutting device operates.

14. In a machine for making sanitary napkins, the combination of a chute pivotally mounted at one end, a cutting device comprising a pair of blades, one blade mounted adjacent the free end of said chute, said free end normally being supported in a plane not lower than the cutting edge of said blade and being adapted to recede when the blades are actuated to sever the work.

15. In a machine for making sanitary napkins, the combination of a wooden chute pivotally mounted at one end, guides on the side of said chute for guiding material thereover, a cutting device comprising a pair of relatively movable blades, one of said blades being mounted adjacent the delivery end of said chute and the other blade being adapted to engage the said guides to depress the delivery end of said chute when the blades are actuated to sever the work and means for yieldingly supporting said delivery end normally in a plane not lower than the cutting edge of the first mentioned blade.

16. In a machine for making sanitary napkins, the combination of means for continuously feeding a strip of wrapping material, means for intermittently advancing a strip of filling material, a cutter operable to sever successive portions of the latter material from the end thereof, means actuated intermittently and independently of the movement of said wrapping and filling material for depositing the severed portions on said strip of wrapping material in spaced relation and means for folding said wrapping material over said filler portions.

17. In a machine for making sanitary napkins, the combination of a frame, means mounted on said frame for feeding a strip of gauze, means for feeding a strip of fibrous, soft, absorbent wadding, and means for severing the forward end portion of said strip of wadding and depositing the severed end portion on said strip of gauze, the last mentioned means including a cutter intermittently operable to sever said end portion, a support for supporting the end portion as it is severed, and mechanism for subsequently effecting relative movement of said support and said end portion.

18. In a machine for making sanitary napkins, the combination of a frame, means mounted on said frame for feeding a strip of gauze, means for feeding a strip of fibrous, soft, absorbent wadding and means for severing the forward end portion of said strip of wadding and depositing the severed end portion on said strip of gauze, the last mentioned means including a cutter intermittently operable to sever said end portion, a support for supporting the end portion as it is severed, mechanism for subsequently effecting relative movement of said support and said end portion and means in the path of movement of said end portion for causing the end portion to be deposited on the strip of gauze, with its side edges substantially parallel to the side edges of the gauze.

19. In a machine for making sanitary napkins, the combination of a frame, means mounted on said frame for continuously feeding a continuous strip of gauze, means for feeding a strip of flat, fibrous, soft, absorbent wadding, and means for severing the forward end portion of said strip of wadding while the latter is horizontally disposed and depositing the severed end portion on said strip of gauze lengthwise of the latter and in horizontal position thereon, the last mentioned means including a cutter intermittently operable to sever said end portion, a support for supporting the end portion in horizontal position until after it is severed, and means for effecting relative movement of said support and the severed portion.

20. In a machine for making sanitary napkins, the combination of a frame, means mounted on said frame for feeding a continuous strip of gauze, means for feeding a strip of fibrous, soft, absorbent wadding, and means for severing the forward end portion of said strip of wadding and depositing the severed end portion on said strip of gauze, the last mentioned means including a cutter intermittently operable to sever said end portion from the strip of wadding, a support for supporting the end portion while it is being severed, and a stripper member movable relative to said support for stripping the severed end portion off said support.

21. In a machine for making sanitary napkins, the combination of a frame, means mounted on said frame for feeding a continuous strip of gauze, means for feeding a strip of fibrous, soft, absorbent wadding, and means for severing the forward end portion of said strip of wadding and depositing the severed end portion of said strip of gauze, the last mentioned means including a cutter intermittently operable to sever said end portion from the strip of wadding, a support for supporting the end portion while it is being severed, a stripper member movable relative to said support for stripping the severed end portion off said support, and means intermediate said support and the strip of gauze, in the path of movement of said end portion for controlling the deposition of said end portion on said gauze.

22. In a machine for making sanitary napkins, the combination of a frame, an endless, flat belt conveyer for feeding a strip of fibrous, soft, absorbent wadding and means for severing end portions from the forward end of said strip of wadding and for depositing the severed end portion on said strip of gauze, the latter means including a cutter intermittently operable to sever such end portions from the strip of wadding, a support for supporting said forward end while it is being severed, and means for stripping the severed portion off said support.

23. In a machine for making sanitary napkins, the combination of a main frame, a belt for supporting a strip of gauze, mechanism for supplying and depositing fibrous, soft, absorbent pads at intervals on the strip of gauze, means acting on the gauze at a point in advance of the locus of deposition of said pads thereon for supplying the gauze to said belt, and folders at opposite sides of the belt for folding the side portions of the gauze inwardly over the belt to enclose the pads deposited thereon.

24. In a machine for making sanitary napkins, the combination of a main frame, a belt for supporting and propelling a strip of gauze, mechanism for supplying and depositing fibrous, soft, absorbent pads at intervals on the strip of gauze, means cooperating with said belt and acting on the gauze at a point in advance of the locus of deposition of said pads thereon for supplying the gauze to said belt, and folders for folding the side portions of the strip of gauze inwardly over the belt to enclose the pads deposited thereon.

25. In a machine for making sanitary napkins, the combination of a conveyer belt for supporting and advancing a strip of gauze, means for supplying and depositing fibrous, soft, absorbent filler pads at intervals on said strip of gauze, a roller acting on said strip of gauze and cooperating with said belt at a point located in advance of the locus of deposition of said pads on the gauze, said roller being yieldably urged toward said belt so as to maintain sufficient frictional contact between the gauze and said belt to enable the latter to draw said gauze strip from a source of supply and to feed said strip forwardly in unison with the travel of the belt, and means for folding marginal side portions of said gauze strip inwardly over the pads.

WILLIAM BAUER.

CERTIFICATE OF CORRECTION.

Reissue No. 21,938. November 11, 1941.

WILLIAM BAUER.

It is hereby certified that error appears in the printed specification of the above numbered patent requiring correction as follows: Page 6, second column, line 52, claim 22, after "an" insert --endless, flat belt conveyer mounted on said frame for continuously propelling a strip of gauze, a second--; and that the said Letters Patent should be read with this correction therein that the same may conform to the record of the case in the Patent Office.

Signed and sealed this 3rd day of March, A. D. 1942.

(Seal)

Henry Van Arsdale,
Acting Commissioner of Patents.